United States Patent
Teraoka et al.

[11] Patent Number: 5,812,240
[45] Date of Patent: Sep. 22, 1998

[54] EYEBALL OBSERVING DEVICE HAVING AN ULTRASONIC DETECTOR

[75] Inventors: Kota Teraoka; Masao Yoshikawa, both of Nagoya, Japan

[73] Assignee: Tomey Corporation, Aichi, Japan

[21] Appl. No.: 537,696

[22] PCT Filed: Feb. 20, 1995

[86] PCT No.: PCT/JP95/00246

§ 371 Date: Oct. 20, 1995

§ 102(e) Date: Oct. 20, 1995

[87] PCT Pub. No.: WO95/23550

PCT Pub. Date: Sep. 8, 1995

[30] Foreign Application Priority Data

Mar. 1, 1994 [JP] Japan .................................. 6-031180

[51] Int. Cl.$^6$ ........................................ A61B 3/14
[52] U.S. Cl. ........................ 351/206; 351/210; 351/212; 396/18
[58] Field of Search .................. 351/205, 206, 351/208, 209, 212, 247, 221, 210; 396/18

[56] References Cited

U.S. PATENT DOCUMENTS

| | | | |
|---|---|---|---|
| 4,764,006 | 8/1988 | Hamano et al. | 351/206 |
| 5,325,135 | 6/1994 | Nakamura et al. | 351/212 |
| 5,337,094 | 8/1994 | Mizuno et al. | 351/206 |

FOREIGN PATENT DOCUMENTS

| | | |
|---|---|---|
| 55-60435 | 5/1980 | Japan . |
| 58-127629 | 7/1983 | Japan . |
| 62-64331 | 3/1987 | Japan . |
| 5-31077 | 2/1993 | Japan . |

*Primary Examiner*—Huy Mai
*Attorney, Agent, or Firm*—Armstrong, Westerman, Hattori, McLeland & Naughton

[57] ABSTRACT

An eyeball observing device comprising an illuminating optical system for illuminating a portin to be examined; a photographing optical system comprising an object lens group equipped with a transparent body which is designed to be in contact with the eyeball and an imaging lens group, the system allowing the image beams coming from the portion to be examined to reach an imaging surface; and a motion picture camera, wherein an ultrasonic oscillator for detecting the position of the examined eye is mounted on the transparent body. The device can provide a clear image of a desired portion of an eyeball quickly.

6 Claims, 4 Drawing Sheets

EYEBALL OBSERVING DEVICE HAVING AN ULTRASONIC DETECTOR

BACKGROUND ART

The present invention relates to an eyeball observing device used for observing eyeball portions and measuring the position thereof. More particularly, it relates to an eyeball observing device in which the leading end of the object lens group comes in contact with the eyeball, the device being used for observing each portion of the eyeball such as retinal, vitreous body, front face of crystalline lens, rear face of crystalline lens, corneal endothelium and corneal epithelium.

For a conventional eyeball observing device, the one disclosed in Japanese Unexamined Patent Publication No. 31077/1993 is known. As shown in FIG. 5, this eyeball observing device 1 comprises an illuminating optical system 7 for illuminating the eye portion to be examined; an eyepiece group 4; a photographing optical system 2 comprising a object lens group 8 provided with a cone lens 15 in contact with the eyeball 6 and an imaging lens group 9 which allow image beams reflected from the eyeball portion to be examined to reach an imaging surface 10; and a motion picture camera 3. Numeral 11 denotes a convex lens group, 12 a concave lens group, 13 a motor for moving the convex lens group 11 along an optical axis, and 14 a rotary encoder for counting number of revolution of the motor 13.

When the image beam reflected from the eye portion to be examined is formed on the imaging surface 10, adjustment is carried out to increase clearness of the image from the motion picture camera 3 by driving the motor 13 to move the convex lens group 11 on the optical axis.

With the above-mentioned conventional eyeball observing device, the examiner moves a part of the imaging lens 9 of the photographing optical system 2 while monitoring the image in order to make the image from the motion picture camera 3 clear. However, because this movement is performed by an electrically connected switch (not shown), it takes time and moreover, during this period, the lamp which illuminates the eyeball to be examined is kept illuminating, thereby creating a problem that a person to be examined is dazzled and is given a large load. Further, every time the eye to be examined moves, the switch must be operated, which also gives a large load to the examiner.

DISCLOSURE OF THE INVENTION

An eyeball observing device according to the present invention comprises an illuminating optical system for illuminating a portion to be examined; a photographing optical system comprising an object lens group equipped with a transparent body which is designed to be in contact with the eyeball and an imaging lens group, the system allowing the image beams coming from the portion to be examined to reach an imaging surface; and a motion picture camera, wherein an ultrasonic oscillator for detecting the position of the eye to be examined is mounted on the transparent body.

The device might be equipped with a moving means for moving at least one of an optical member of the photographing optical system and a motion picture camera on the optical axis based on detection results of the position of the eye to be examined which have been detected by the ultrasonic oscillator.

According to the present invention, since an ultrasonic oscillator for detecting the position of the eye to be examined is equipped to the transparent body in contact with the eyeball in the object lens group, only by measuring the time in which ultrasonic generated from the ultrasonic oscillator is reflected at the object and returns, quick and accurate detection of the position of a desired portion can be achieved. If the examiner adjusts manually or electrically the photographing optical system and the like based on this detection result of the position in such a manner to form an image on the imaging surface, the image of the desired portion can be obtained quickly and clearly.

BEST MODE FOR CARRYING OUT THE INVENTION

The eyeball observing device according to the present invention will be described in detail referring to the attached drawings.

Figure 1:
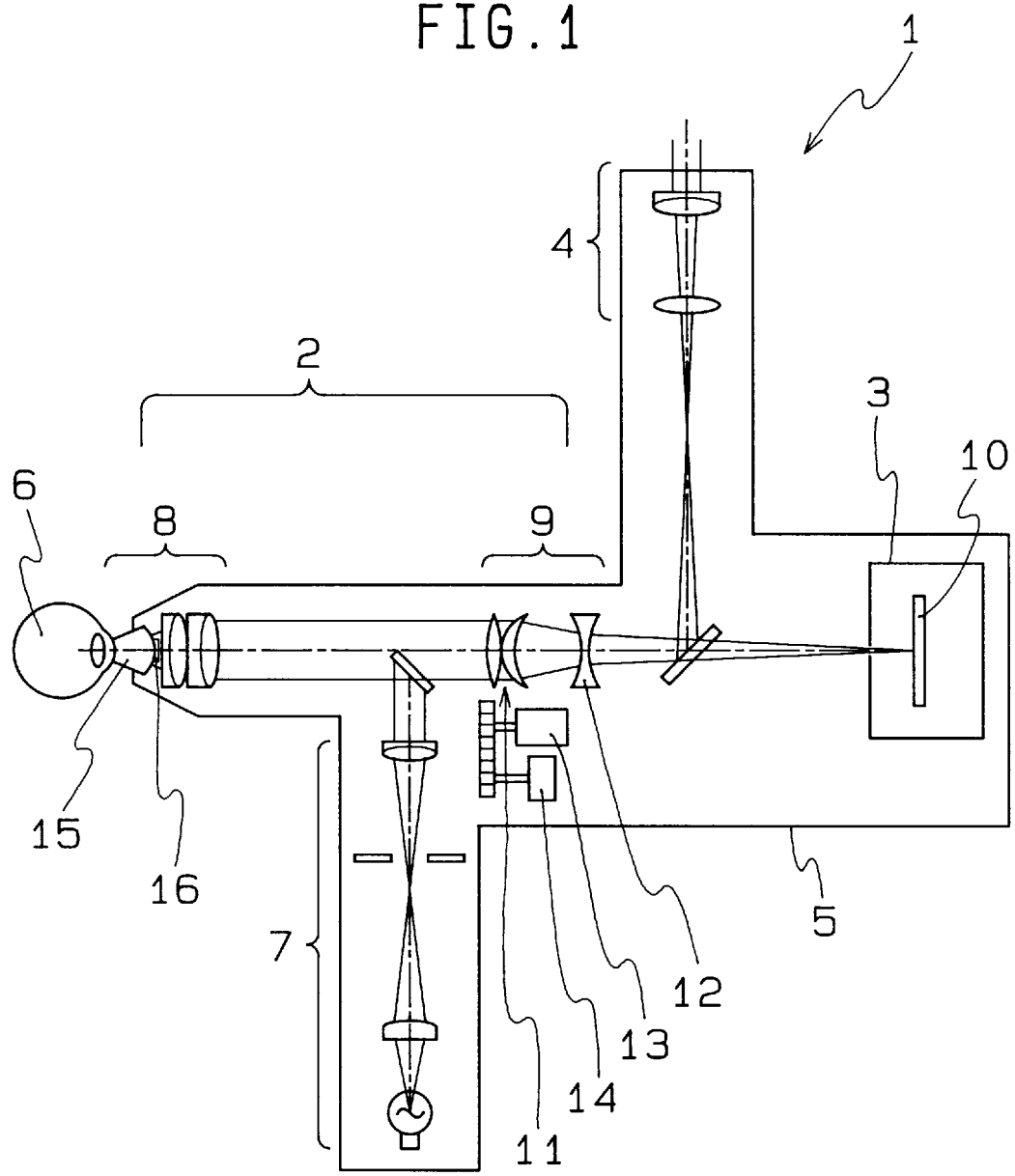
FIG. 1 is a schematic representation of an optical path showing an embodiment of an eyeball observing device according to the present invention.
Figure 5:
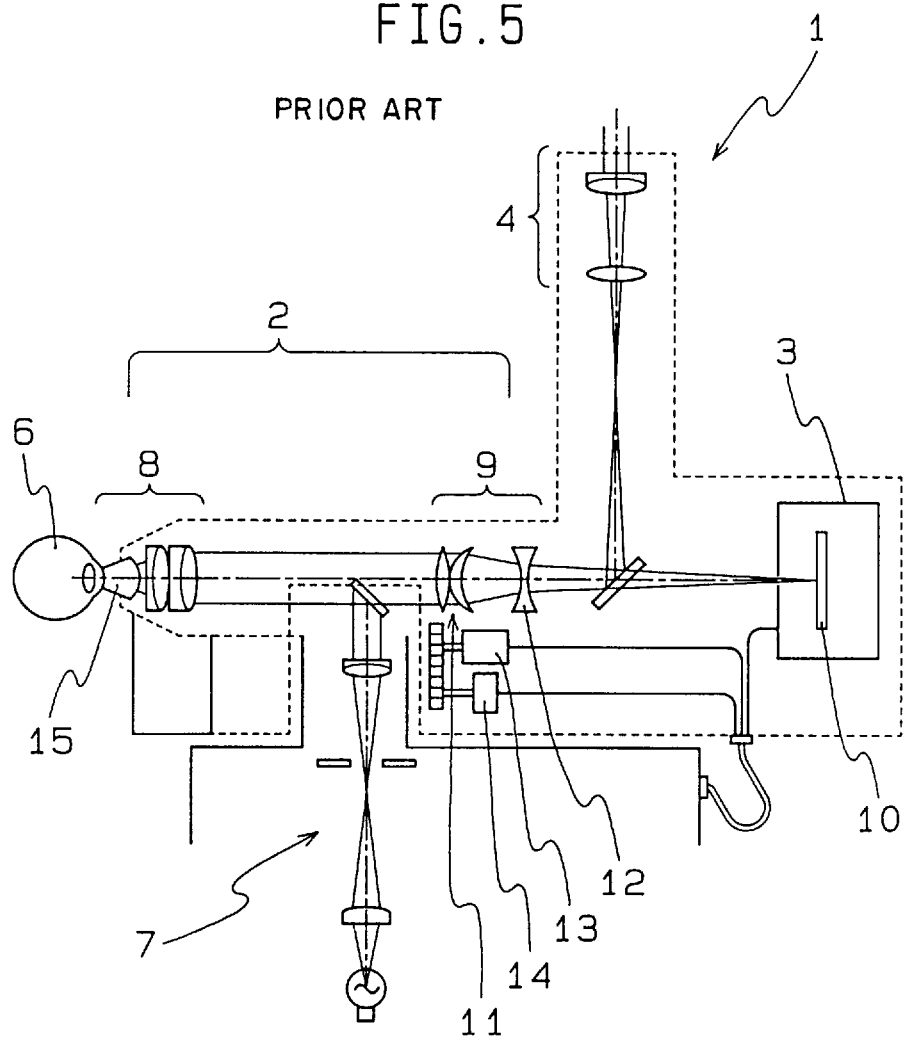
FIG. 5 is a schematic representation of an optical path of a conventional eyeball observing device.

In FIG. 1, numeral 1 denotes an eyeball observing device, comprising an illuminating optical system 7 for illuminating the eyeball 6; an eyepiece group 4 for visually observing the examined eye directly; a photographing optical system 2 comprising an object lens group 8 equipped with a transparent body, for example, cone lens 15 which is designed to be in contact with the eyeball 6, and an imaging lens group 9, the system allowing the image beams coming from the eyeball 6 to reach an imaging surface; and a motion picture camera 3. Numerals 11–14 are elements same as those shown by numerals 11–14 in FIG. 5. To the cone lens 15, an ultrasonic oscillator 16 is mounted on the surface on the motion picture camera side of the cone lens 15 to face the eyeball 6 by, for example, being adhered closely to the surface.

The photographing optical system 2, motion picture camera 3, eyepiece group 4, and illuminating optical system 7 (that is, all photographing means) are contained in a case 5. The case 5 which contains the all photographing means is supported on the main body frame (not shown) in such a manner that it can move (full floating) along the optical axis of the photographing optical system 2.

It might be designed, in place of full floating mechanism, to fix the case 5 to the main body frame and allow only the object lens group 8 of the photographing optical system to move.

Figure 2:
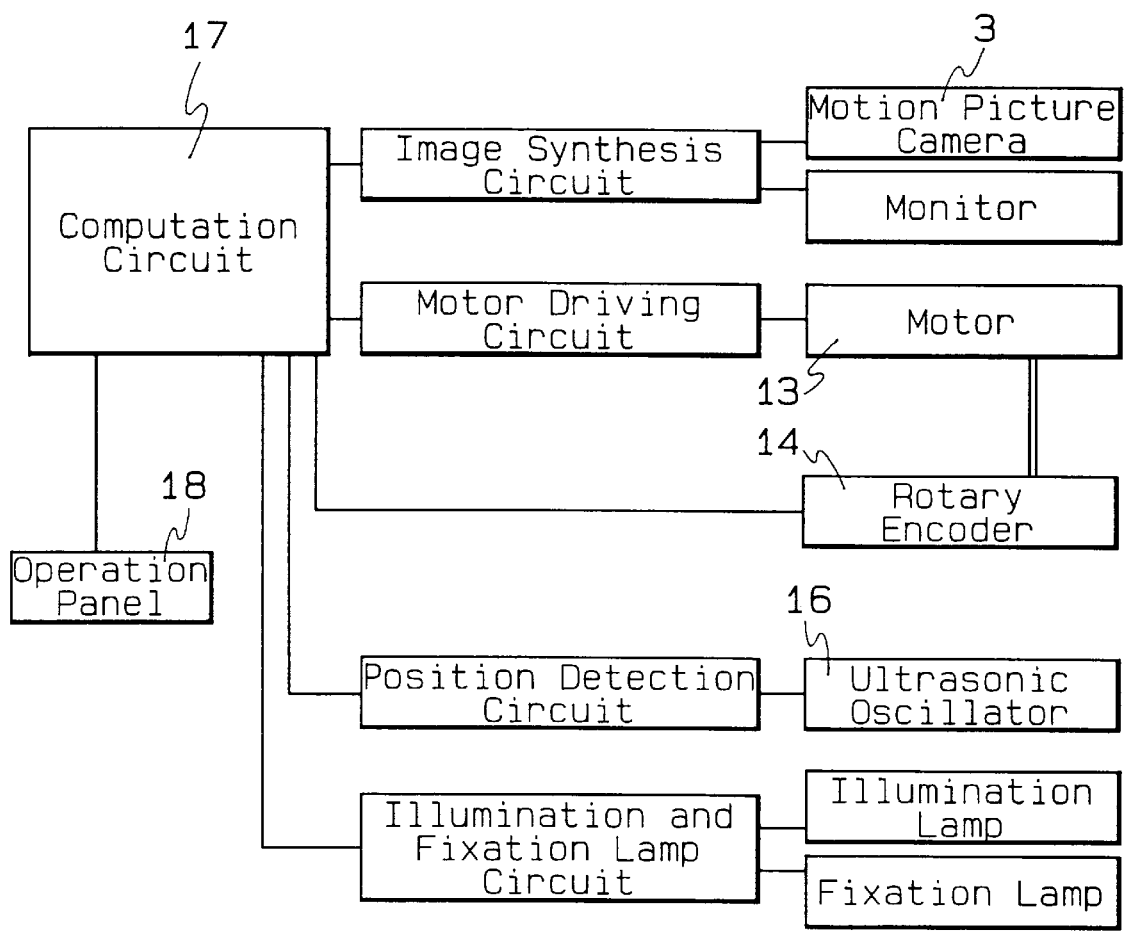
FIG. 2 is a block diagram showing a system configuration of the eyeball observing device of FIG. 1.

The imaging lens group 9 forms an image of the image beams passing through the object lens group 8 on the imaging surface 10 in the motion picture camera 3 on the optical axis, and comprises a convex lens group (object lens 8 side) 11 and a concave lens group (imaging surface 10 side) 12 which are provided with a clearance therebetween. The convex lens group 11 is designed to be movable on the optical axis by using the driving force of the motor 13 and has focusing function The system of the eyeball observing device 1 is configured as shown in FIG. 2.

For an ultrasonic oscillator 16, a piezoelectric member such as a ceramic oscillator and a high-molecular oscillator which can convert mechanical energy to electrical energy and vice versa is used, and, for example, in observing and measuring cornea, there can be adopt a piezoelectric member having a measuring range of 0–2000 μm, measuring accuracy of ±5 μm, and oscillation frequency of about 10–30 MHz.

The ultrasonic oscillator 16 is mounted on the motion picture camera side of the cone lens 15. By selecting plastic lens made of material with good ultrasonic transparency such as polycarbonate and PMMA, and closely adhering the ultrasonic oscillator 16 on the surface of the cone lens 15 by adhesive, detection of the eyeball position can be made without trouble even if a cone lens is intervened.

By fixing the illuminating beams to the eye to be examined and allowing ultrasonic waves to move on the visual axis, echoes can be obtained from corneal epithelium, corneal endothelium, front face of crystalline lens and rear face of crystalline lens in this order. Thus, by setting the positional relationship in advance as shown in Table 1, the position of a desired portion of the eyeball to be examined can be selectively detected.

Figure 3:
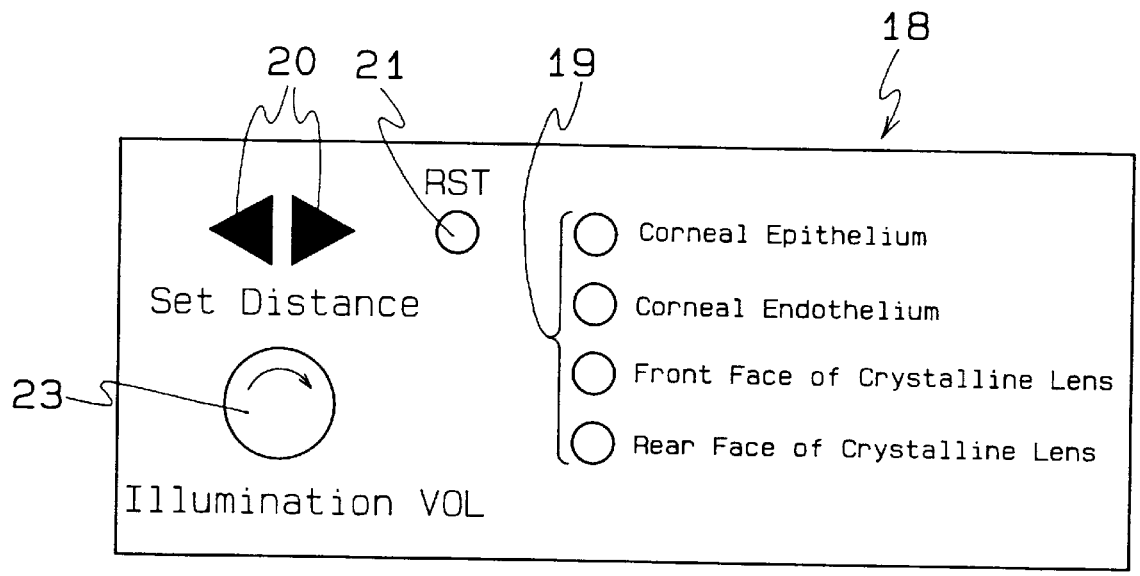
FIG. 3 is a schematic representation of an operation panel with an operation switch in the eyeball observing device of FIG. 1.

In order to allow an image of the desired portion to be formed on the imaging surface 10, first of all, the portion to be examined is chosen by operating the selector switch 19 on the operation panel 18 in FIG. 3. When chosen, the set distance inputted in advance from the portion to be examined to the leading end of the cone lens 15 is computed by a computation circuit 17 shown in FIG. 2, and based on this set distance, the convex lens group 11 moves on the optical axis thereof.

The relationship between each portion to be examined and set distance (distance from the cone lens) is given as shown in Table 1.

TABLE 1

| Portion to be examined | Set distance (mm) |
| --- | --- |
| corneal epithelium | 0–0.2 |
| corneal endothelium | 0.2–1 |
| front face of crystalline lens | 1.0–5.0 |
| rear face of crystalline lens | 6.0–9.0 |

For example, by choosing the switch "corneal endothelium" on the operation panel 18 in FIG. 3, the set distance LO=550 μm (sum of the thickness 50 μm of cornea protecting liquid inputted in advance and the distance 500 μm from corneal epithelium to corneal endothelium) is computed, the convex lens group 11 moves on the optical axis, and the image located at the position 550 μm ahead from the leading end of the cone lens 15 forms on the imaging surface 10, thereby a clear picture is projected.

Now, description will be made on the method for observing the eyeball and measuring the eyeball position using the eyeball observing device according to the present invention.

Figure 4:
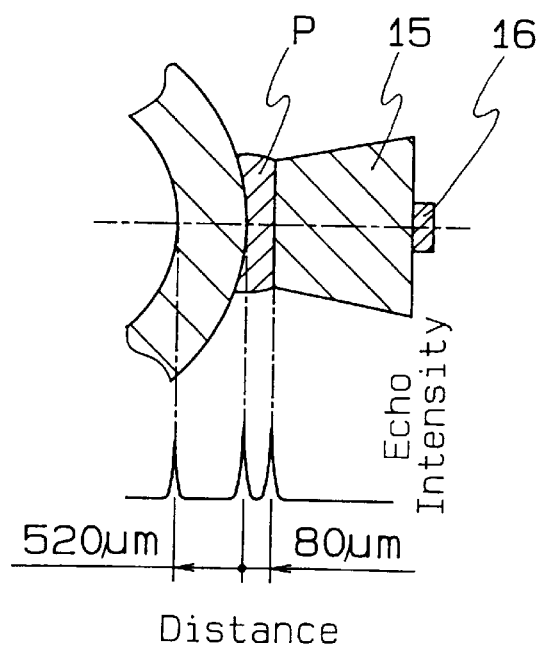
FIG. 4 is an explanatory view showing relationship between distance from the ultrasonic oscillator in FIG. 1 and echo intensity.

First of all, a cornea protecting liquid P is dripped to a cornea of an eye to be examined and then, the whole case 5 is moved to the eyeball 6 side to allow the cone lens 15 of the eyeball observing device to come into contact with the cornea. Then, the switch "corneal endothelium" is chosen from setting switches 19 and turned on, and ultrasonic waves are oscillated from the ultrasonic oscillator 16 mounted on the motion picture camera side of the cone lens 15, thereby the echo shown in FIG. 4 is detected. In that case, the cornea thickness, that is, distance from the corneal epithelium to the corneal endothelium (520 μm) is simultaneously measured and displayed on a monitor (not shown). Based on the detection results, the distance L=600 μm from the leading end of the cone lens 15 to the corneal endothelium (sum of the measured thickness of cornea protecting liquid of 80 μm and the distance 520 μm from the corneal epithelium to the corneal endothelium) is computed in the arithmetic circuit 17. In addition, it is compared with the set distance LO=550 μm to compute the difference, and in accordance with the value, the required number of revolutions of the motor 13 for moving the convex lens group 11 along the optical axis is computed. Then, the motor 13 is rotated to move the convex lens group 11 along the optical axis and to adjust the focus. When the specified number of revolutions is counted by a rotary encoder 14, which is a means for detecting the number of revolutions, the motor 13 stops rotating. As a result, the convex lens group 11 is positionally adjusted in accordance with the actually measured distance L, so that accurate focusing can be performed, resulting in a clear image of the corneal endothelium. Since L>LO in the above-mentioned case, the convex lens group 11 moves to the imaging surface 10 side. On the other hand, if L<LO, it moves to go away from the imaging surface 10.

The operation panel of FIG. 3 is equipped with a set distance changing switch 20 to enable input of a various kinds of portions to be examined. When changing the setting, for example, after pressing the setting switch 19 for desired setting, the reset button 21 is pressed, and then the change switch 20 is operated to change the set distance.

The brightness of the lamp which illuminates the eye to be examined can be appropriately adjusted by operating the illuminating light volume controller. The illuminating light might be kept illuminating (flash) only at the time of taking photos.

In this embodiment, the convex lens group 11 of the imaging lens group 9 is moved on the optical axis by using the moving means such as a rotating motor 13, but other optical members of the photographing optical system 2 on the optical axis (for example, the concave lens group 12, or a part of the object lens group 8) or a motion picture camera 3 might be moved.

It is also possible to adjust the focus by appropriately changing the optical distance by using, as a moving means, a piezoelectric actuator or an electromagnetic-magnetic linear motor which generates linear driving force.

According to the present invention, since an ultrasonic oscillator for detecting the portion to be examined is mounted on the transparent body of the object lens group in contact with the eyeball, a clear image of a desired portion can be quickly obtained based on this position detection result.

Consequently, a person to be examined can get rid of glare caused by continuously watching the illuminating light. On the other hand, the examiner can obtain an excellent effect of observing clear images without operating anything. Moreover, it is very significant from the clinical viewpoint that both the image of the corneal endothelium, which is a portion to be examined, and cornea thickness can be obtained simultaneously and quickly.

The eyeball observing device according to the present invention has two functions of eyeball observation and eyeball position measurement, achieving effects on space saving in hospitals and institutions.

INDUSTRIAL APPLICABILITY

The eyeball observing device according to the present invention can produce images of the observed portion of various eyeball portions clearly and quickly and at the same time measure the eyeball position. Accordingly, it can be applied for inspections in ophthalmic treatments such as the inspection before and after corneal refraction correction operations or for collection of data which serves as data for selecting intraocular lens.

We claim:

1. An eyeball observing device comprising:
   an illuminating optical system for illuminating a portion to be examined;
   a photographing optical system including an object lens group equipped with a transparent body which is designed to be in contact with the eyeball and an imaging lens group, the photographing optical system allowing image beams coming from the portion to be examined to reach an imaging surface;
   a camera; and
   an ultrasonic oscillator for detecting the position of the eye to be examined mounted on the transparent body; wherein
   said transparent body has ultrasonic transparency, said ultrasonic oscillator detects the position of the eye to be examined using ultrasonic waves transmitted through said transparent body and said camera is operated in response to the position of the eye to be examined detected by said ultrasonic oscillator.

2. The device of claim 1, wherein the device further includes a moving means for moving at least one of an optical member of the photographing optical system and a camera on the optical axis based on detection results of the position of the eye to be examined which have been detected by the ultrasonic oscillator.

3. The device of claim 1, wherein said ultrasonic oscillator is mounted on the camera side of said transparent body.

4. The device of claim 1, wherein said photographing system photographs said eye to be examined simultaneously with the detection of the position of the eye to be examined by said ultrasonic oscillator.

5. The device of claim 1, wherein said photographing optical system focuses a desired part of the eye to be examined simultaneously with operating said ultrasonic oscillator and in response to the position measured by said ultrasonic oscillator.

6. The device of claim 1, wherein said camera is a motion picture camera.

* * * * *